United States Patent [19]

Kohl

[11] Patent Number: 5,475,111

[45] Date of Patent: Dec. 12, 1995

[54] PROCESS FOR THE PREPARATION OF DIHYDROPYRIDINECARBOXYLIC ACIDS

[75] Inventor: Bernhard Kohl, Konstanz, Germany

[73] Assignee: BYK Gulden Lomberg Chemische Fabrik GmbH, Konstanz, Germany

[21] Appl. No.: 81,332

[22] PCT Filed: Dec. 20, 1991

[86] PCT No.: PCT/EP91/02476

§ 371 Date: Aug. 17, 1993

§ 102(e) Date: Aug. 17, 1993

[87] PCT Pub. No.: WO92/11239

PCT Pub. Date: Jul. 9, 1992

[30] Foreign Application Priority Data

Dec. 24, 1990 [DE] Germany ............ 40 41 814.6

[51] Int. Cl.$^6$ ............ C07D 211/90

[52] U.S. Cl. ............ 546/322; 546/270; 546/271; 546/321

[58] Field of Search ............ 546/322, 270, 546/271, 321

[56] References Cited

U.S. PATENT DOCUMENTS 4,769,465  9/1988  Antoncic et al. ............ 546/321

FOREIGN PATENT DOCUMENTS

| | | | |
|---|---|---|---|
| 0249245 | 12/1987 | European Pat. Off. | 546/322 |
| 0296316 | 12/1988 | European Pat. Off. | 546/322 |
| 3809912 | 10/1988 | Germany | 546/322 |
| 2122192 | 1/1984 | United Kingdom | 546/322 |
| WO88/07531 | 10/1988 | WIPO | 546/322 |
| WO88/07524 | 10/1988 | WIPO | 546/322 |
| WO88/09331 | 12/1988 | WIPO | 546/322 |

OTHER PUBLICATIONS

Chemistry of heterocyclic compounds, vol. 14, No. 2, Feb. 1978, p. 225.
Chem. Pharm. Bull. vol. 28, No. 9, 1980, pp. 2809–2812.
Chem. Pharm. Bull 37(8), 1989, pp. 2225–2228.

*Primary Examiner*—C. Warren Ivy
*Assistant Examiner*—Zinna N. Davis
*Attorney, Agent, or Firm*—Jacobson, Price, Holman & Stern

[57] ABSTRACT

The invention relates to a process for the preparation of optically pure 1,4-dihydropyridinemonocarboxylic acids of the formula I

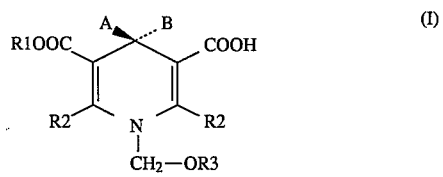

in which the substituents have the meanings mentioned in the description.

10 Claims, No Drawings

PROCESS FOR THE PREPARATION OF DIHYDROPYRIDINECARBOXYLIC ACIDS

This application is a 371 of PCT/EP91/02476 filed Dec. 20, 1991.

AREA OF APPLICATION OF THE INVENTION

The invention relates to a novel process for the preparation of dihydropyridinecarboxylic acids. The compounds prepared according to the invention are employed as precursors in the pharmaceutical industry.

KNOWN TECHNICAL BACKGROUND

Since the fact was made known that, in the area of calcium antagonists of the 1,4-dihydropyridine type, in the case of chiral compounds one enantiomer usually has a distinctly more strongly pronounced cardiovascular action that the other, the need for a suitable, stereoselective synthesis or for a resolution into the enantiomers which also works on the industrial scale has continuously grown. This is seen in the multiplicity of publications and published patent applications, in which resolutions or enantioselective syntheses of chiral 1,4-dihydropyridinecarboxylic acid derivatives are described.

In D. Enders et al. [Tetrahedron Letters 29, 6437 (1988)], an enantioselective synthesis of 1,4-dihydropyridine is described in which the intermediate condensation with a chiral hydrazine leads to a product which is greatly enriched (84 to 98% purity) in one enantiomer. B. Lamm and R. Simonsson [Tetrahedron Letters 30, 6423 (1989)] describe the resolution of felodipine into the enantiomers with the aid of an optically active alcohol. In attempts to obtain manidipine [Drugs of the future 15, 311 (1990)] or alternatively other pharmacologically interesting 1,4-dihydropyridines [such as, e.g., YM-09730, J. Med. Chem. 29, 2504 (1986)] in optically pure form, the synthesis has usually still been carried out recently by the method described in Shibanuma et al. [Chem. Pharm. Bull. 28, 2809 (1980)], in which the monocarboxylic acid regarded as the key compound is prepared from the diester by hydrolysis using sodium 1-dimethylamino-2-propanolate and 2% water. Novel routes to corresponding monocarboxylic acids are described in International Patent Applications WO88/07524 and WO88/09931.

DESCRIPTION OF THE INVENTION

Surprisingly, a route which is particularly problem-free and can easily be used on the industrial scale for the preparation and processing of the 1,4-dihydropyridinemonocarboxylic acids described in Shibanuma et al. (see above) and regarded as key intermediates has now been found. The invention thus relates to a process for the preparation of optically pure 1,4-dihydropyridinemonocarboxylic acids of the formula I

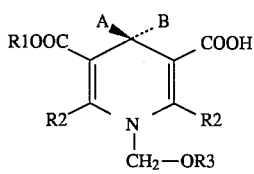

in which
R1 denotes 1–4C-alkyl,
R2 denotes 1–4C-alkyl,
R3 denotes 1–4C-alkyl or benzyl, and either
A denotes hydrogen and
B denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical, or
A denotes a 2-chlorophenyl, 3-chlorophenyl, 2,3-dichlorophenyl, 2-nitrophenyl, 3-nitrophenyl, benzoximidazolyl (4-benzofurazanyl), 2-trifluorobenzoimidazolyl (4-benzofurazanyl), 2-trifluoromethylphenyl, 2,3-methylenedioxyphenyl or 2-difluoromethoxyphenyl radical and
B denotes hydrogen.

The process in a first aspect comprises hydrolysing a compound of the formula II

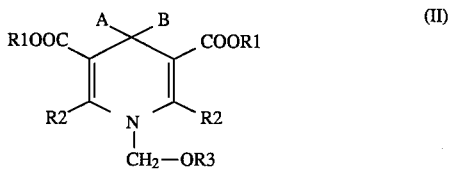

in which R1, R2, R3, A and B have the abovementioned meanings, in an alcohol R1—OH using aqueous alkali metal hydroxide and resolving the resultant acid III

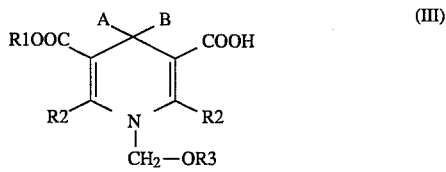

into the enantiomers in the customary manner. In a further aspect, the process comprises employing the undesired enantiomer, after ester formation with the compound R1—X in which R1 has the abovementioned meaning and X represents a leaving group or a halocarbonyloxy group, again as the starting compound II.

1–4C-alkyl represents methyl, ethyl, propyl, butyl, isopropyl, isobutyl, sec-butyl and tert-butyl. Preferred 1–4C-alkyl radicals R1 are isobutyl, isopropyl and in particular ethyl and methyl. Preferred 1–4C-alkyl radicals R2 are ethyl and methyl. A preferred 1–4C-alkyl radical R3 is ethyl.

The hydrolysis in the alcohol R1—OH is advantageously carried out at a dilution ratio (compound II:alcohol) of 1:3 to 1:40, preferably 1:5 to 1:10.

A suitable aqueous alkali metal hydroxide is in particular 0.3- or 10-molar, preferably 0.5- to 2-molar, sodium hydroxide solution or potassium hydroxide solution, where—relative to the compound II—0.9 to 1.5 equivalents, preferably 0.95 to 1.20 equivalents, in particular 1.0 equivalent, of alkali metal hydroxide is employed.

The hydrolysis is preferably carried out at temperatures between 50° and 120° C., in particular at the boiling point of the alcohol R1—OH used.

The acid III formed by the hydrolysis, which is present as a racemate, can be resolved into the enantiomers in a customary manner via the diastereomeric salts using enantiomerically pure, optically active bases [see, e.g., Chem. Parm. Bull. 28, 2809 (1980)].

The undesired or unrequired optically pure acid III is esterified with the compound R1—X in a manner familiar per se to the person skilled in the art. The leaving group X of the compound R1—X is a group which is easily removed during the ester formation, for example a halogen atom, such as chlorine, bromine or iodine, or preferably the alkylsulfate group. X is just as preferably a halocarbonyloxy group, in particular the chlorocarbonyloxy group, such that the compound R1—X is an alkyl chloroformate.

The reaction of the compound III with the compound R1—X is preferably carried out under basic conditions, preferably in the presence of a phase transfer catalyst. Catalysts which may be mentioned in addition to onium salts, such as e.g., tetrabutylammonium bromide or benzyltriethylammonium chloride, are especially crown ethers, such as dibenzo-[18]crown-6, dicyclohexyl[18]crown-6 and in particular [18]crown-6.

Possible bases, which are employed at least in a molar ratio, preferably in excess, are inorganic bases, such as alkali metal hydroxides (e.g. sodium hydroxide or potassium hydroxide), or in particular alkali metal carbonates, (e.g. sodium carbonate or preferably potassium carbonate). When working in an anhydrous solvent, the hydroxides or carbonates used are preferably employed in finely powdered form.

The reaction is carried out (depending on the type of phase transfer catalyst and the base employed) in water-containing or anhydrous organic solvents, or in a mixture of water and an organic solvent which is immiscible or hardly miscible with water. Water/solvent mixtures which may be mentioned are, for example, the mixtures of water with chloroform, dichloromethane or toluene. Water-containing or anhydrous solvents which may be mentioned are, for example, dichloromethane, acetonitrile or in particular acetone, methyl ethyl ketone or methyl isobutyl ketone.

The reaction is carried out (depending on the type of compound R1—X employed) at temperature between 20° and 150° C., where, for example, in the reaction with dimethyl sulfate temperatures between 20° and 60° C. and in the reaction with methyl chloroformate temperatures between 50° and 120° C. are preferred.

An embodiment of the invention (embodiment a) relates to a process for the preparation of optically pure 1,4-dihydropyridinecarboxylic acids of the formula Ia

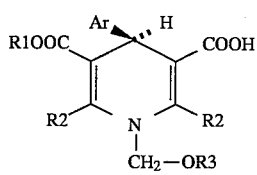
(Ia)

in which
R1 denotes 1–4C-alkyl,
R2 denotes 1–4C-alkyl,
R3 denotes 1–4C-alkyl or benzyl and
Ar denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical.

The process comprises hydrolysing a racemate of the formula IV

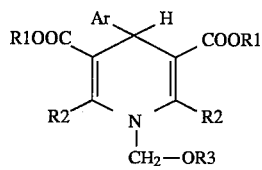
(IV)

in which R1, R2, R3 and Ar have the abovementioned meanings, in an alcohol R1—OH using aqueous alkali metal hydroxide, resolving the resultant racemic acid V

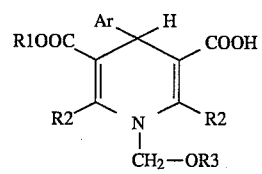
(V)

in a customary manner into the enantiomers Ia and Ib

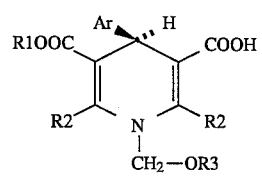
(Ia)

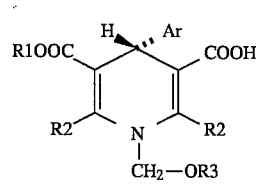
(Ib)

and employing the enantiomer Ib, after ester formation with the compound R1—X in which R1 has the abovementioned meaning and X represents a suitable leaving group or a halocarbonyloxy group, again as the starting compound IV.

A further embodiment of the invention (embodiment b) relates to a process for the preparation of optically pure 1,4-dihydropyridinecarboxylic acids of the formula Ib

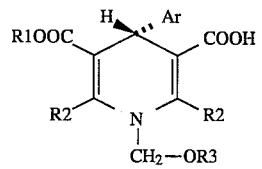
(Ib)

in which
R1 denotes 1–4C-alkyl,
R2 denotes 1–4C-alkyl,
R3 denotes 1–4C-alkyl or benzyl and
Ar denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical.

The process comprises hydrolysing a racemate of the formula IV

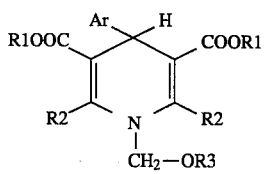

in which R1, R2, R3 and Ar have the abovementioned meanings, in an alcohol R1—OH using aqueous alkali metal hydroxide, resolving the resultant racemic acid V

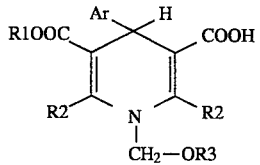

in a customary manner into the enantiomers Ia and Ib

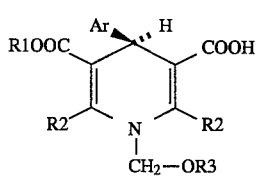

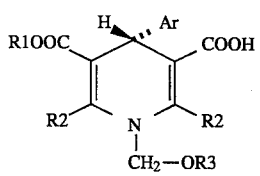

and employing the enantiomer Ia, after ester formation with the compound R1—X in which R1 has the abovementioned meaning and X represents a suitable leaving group or a halocarbonyloxy group, again as the starting compound IV.

Preferred compounds prepared by the processes of embodiments a and b are those of the formulae Ia and Ib, in which R1 denotes 1–4C-alkyl, R2 denotes 1–4C-alkyl, R3 denotes 1–4C-alkyl, and Ar denotes 3-nitrophenyl or 2,3-dichlorophenyl.

Particularly preferred compounds prepared by the processes of embodiments a and b are those of the formulae Ia and Ib, in which R1 denotes methyl or ethyl, R2 denotes methyl, R3 denotes ethyl and Ar denotes 3-nitrophenyl.

The following examples illustrate the invention in greater detail. M.p. represents melting point, h represents hour(s) and min represents minute(s).

EXAMPLES

1. (±)-1-Ethoxymethyl-1,4-dihydro-5-methoxycarbonyl-2,6-dimethyl-4-(3-nitrophenyl)pyridine-3-carboxylic acid a) 50 g (0.124 mol) of dimethyl (±)-1-ethoxymethyl-1,4-dihydro-2,6-dimethyl-4-(3-nitrophenyl)pyridine-3,5-dicarboxylate are heated to boiling under reflux for 24 h in 500 ml of methanol after addition of 136 ml of 1N potassium hydroxide solution. After distilling off 350 ml of methanol, 300 ml of water are added. The mixture is clarified with the addition of 5 g of active carbon, 2N hydrochloric acid is added dropwise to the filtrate to pH 3, and the precipitated solid is filtered off, washed with water until chloride-free and dried to constant weight (40° C./vacuum. 44 g (91% of theory) of the title compound of m.p. 182°–183° C. are obtained.

b) The title compound is also obtained if in procedure 1a) the 1N potassium hydroxide solution is replaced by the same amount of 1N sodium hydroxide solution. Yield: 40 g (83% of theory) of beige powder. After stirring in 300 ml of hot methanol, 34.4 g (71%) of the title compound of m.p. 184°–185° C. are obtained.

c) The title compound is also obtained if in procedure 1a) the 1.1 equivalents of 1N potassium hydroxide solution are replaced by 1.3 equivalents of 4N potassium hydroxide solution. Starting from 5.15 g of dimethyl ester, in this case 4.0 g (83% of theory) of the title compound of m.p. 177°–178° C. are obtained.

2. (±)-1-Ethoxymethyl-1,4-dihydro-5-ethoxycarbonyl-2,6-dimethyl-4-(3-nitrophenyl)pyridine-3-carboxylic acid By the procedure described in Example 1a), 1.4 g (75% of theory) of the title compound m.p. 188°–189° C. are obtained as a beige crystal powder from 2 g of diethyl (±)-1-ethoxymethyl-1,4-dihydro-2,6-dimethyl-4-(3-nitrophenyl)pyridine-3,5-dicarboxylate in 20 ml of ethanol using 5.1 ml (1 mmol) of 1N potassium hydroxide solution (1.1 equivalents) after 40 h under reflux and with identical working up.

3. (±)-4-(2,3-Dichlorophenyl-1-ethoxymethyl-1,4-dihydro-2,6-dimethyl-5-methoxycarbonylpyridine-3-carboxylic acid By the procedure described in Example 1a), 1.4 g (72% of theory) of the title compound of m.p. 168°–169° C. are obtained from 2 g (4.7 mmol) of dimethyl (±)-4-(2,3-dichlorophenyl)-1-ethoxymethyl-1,4-dihydro-2,6-dimethyl-pyridine-3,5-dicarboxylate in 20 ml of methanol containing 5.2 ml of 1N potassium hydroxide solution after 60 h under reflux and with identical working up.

4. Dimethyl (±)-1-ethoxymethyl-1,4-dihydro-2,6-dimethyl-4-(3-nitrophenyl)pyridine-3,5-dicarboxylate a) 280 g (0.717 mol) of the acid which is no longer required after the resolution of the racemate are suspended in 3 l of acetone; 300 g of powdered potassium carbonate and 1 g of [18]crown-6 are added and 71.5 ml (0.75 mol) of dimethyl sulfate are added dropwise at 25° C. with stirring in the course of 1 hour. After a stirring time of 5 h (internal temperature 25°–30° C.), 30 ml of triethylamine are added to remove excess dimethyl sulfate and the mixture is allowed to react to completion for 18 h. It is then filtered, the filtrate is concentrated in vacuo in a rotary evaporator and the residue is crystallized by addition of diisopropyl ether. 244 g (84% of theory) of dimethyl (±)-1-ethoxymethyl-1,4-dihydro-2,6-dimethyl-4-(3-nitrophenyl)pyridine-3,5-dicarboxylate are obtained in the form of beige crystals of m.p. 86°–88° C.

b) The title compound is also obtained by the following process: 30 g (77 mmol) of the acid which is no longer required after the resolution of the racemate are heated at reflux temperature for 2 hours together with potassium carbonate (31 g, 231 mmol), methyl chloroformate (7.6 g, 85 mmol) and [18]crown-6 (0.3 g) in 400 ml of isobutyl methyl ketone. After cooling to 20° C., inorganic salts are filtered off and the filtrate is completely concentrated. The oily residue is crystallized from methanol/water. The title compound (25 g; 80% of theory) is obtained in the form of a beige crystal powder; m.p. 85°–87° C.

TECHNICAL APPLICABILITY

A process is made available by means of the invention by which enantiomerically pure 5-alkoxycarbonyl-1,4-dihydropyridine-3-carboxylic acids, which are required as useful intermediates for the synthesis of enantiomerically pure, pharmacologically active 1,4-dihydropyridine-3,5-dicarboxylic acid diesters, can be prepared by a simple route and in high yield.

In Sausin et al. (Khimiya Geterotsiklicheskikh Soedinenii, No. 2, p. 272, February 1978) the partial hydrolysis of N-alkylated dialkyl 1,4-dihydropyridinedicarboxylates using potassium hydroxide solution is admittedly described, and in European Patent Application 202,652 the partial hydrolysis of N-unsubstituted dialkyl 1,4-dihydropyridinedicarboxylates is reported. These publications, however, have not suggested to the person skilled in the art to attempt the partial hydrolysis of a dialkyl 1,4-dihydropyridinedicarboxylate, which carries on the nitrogen a protective group which is easily removable in principle (such as, e.g., in this case —CH$_2$—OR$_3$). Had the partial hydrolysis according to the invention actually been suggested, then it would have been employed a long time ago in the heavily researched area of the 1,4-dihydropyridines. However, this is not the case. The recent publications, in which the synthesis of enantiomerically pure 1,4-dihydropyridinemonocarboxylic acids as intermediates is described, refer rather to the substantially more involved and complicated synthesis according to Shibanuma et al. (see above). The process according to the invention thus does not follow in an obvious manner from the prior art for the person skilled in the art.

In addition to the hydrolysis of the diester to the monoester, which proceeds in high yields and is completely straightforward, the recycling of the unrequired chiral monoester to the non-chiral diester is a further important aspect of the process. As a result of the "racemization" of the unrequired compound (which otherwise would have to be disposed of) and its reintroduction into the preparation cycle, the preparation costs for the desired final product are distinctly reduced.

The processing of the intermediates prepared by the process according to the invention to give pharmacologically active final products is described, for example, in International Patent Applications WO88/07524 and WO88/07525.

I claim:
1. A process for the preparation of an optically pure 1,4-dihydropyridinemonomcarboxylic acid of formula I

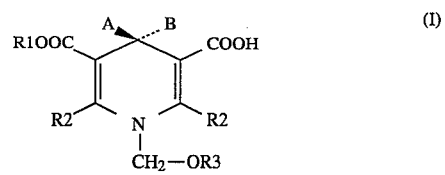

in which
R1 denotes 1–4C-alkyl,
R2 denotes 1–4C-alkyl,
R3 denotes 1–4C-alkyl or benzyl, and either
A denotes hydrogen and
B denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical, or
A denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical and
B denotes hydrogen,
which comprises hydrolysing a compound of the formula II

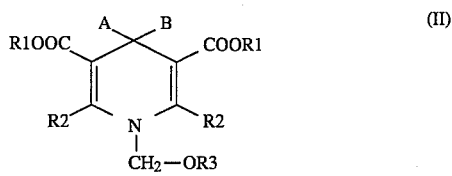

in which R1, R2, R3, A and B have the abovementioned meanings, in an alcohol R1—OH using aqueous alkali metal hydroxide, resolving the resultant acid III

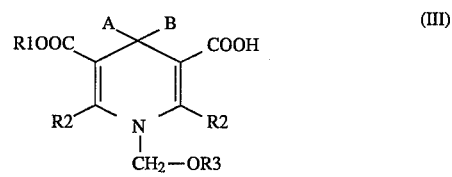

into the enantiomers in a customary manner and employing the undesired enantiomer, after ester formation with the compound R1—X having the abovementioned meaning throughout this claim and X representing a leaving group or a halocarbonyloxy group, again as the starting compound II.

2. The process as claimed in claim 1, for the preparation of an optically pure 1,4-dihydropyridinecarboxylic acid of the formula Ia

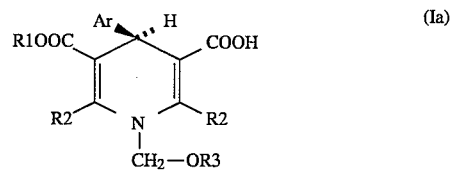

in which
R1 denotes 1–4C-alkyl,
R2 denotes 1–4C-alkyl,

R3 denotes 1–4C-alkyl or benzyl and

Ar denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical, which comprises hydrolysing a racemate of the formula IV

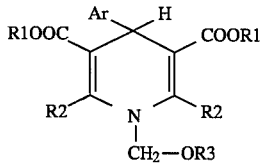

(IV)

in which R1, R2, R3 and Ar have the abovementioned meanings, in an alcohol R1—OH using aqueous alkali metal hydroxide, resolving the resultant racemic acid V

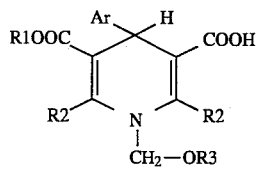

(V)

in a customary manner into the enantiomers Ia and Ib

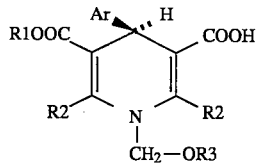

(Ia)

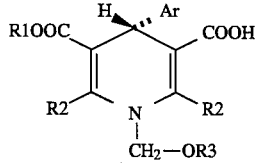

(Ib)

and employing the enantiomer Ib, after ester formation with the compound R1—X, in having the abovementioned meaning throughout this claim and X representing a suitable leaving group or a halocarbonyloxy group, again as the starting compound IV.

3. The process as claimed in claim 1 for the preparation of an optically pure 1,4-dihydropyridinecarboxylic acid of the formula Ib

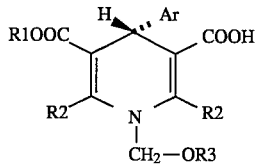

(Ib)

in which

R1 denotes 1–4C-alkyl,

R2 denotes 1–4C-alkyl,

R3 denotes 1–4C-alkyl or benzyl and

Ar denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical, which comprises hydrolysing a racemate of the formula IV

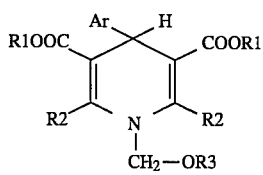

(IV)

in which R1, R2, R3 and Ar have the abovementioned meanings, in an alcohol R1—OH using aqueous alkali metal hydroxide, resolving the resultant racemic acid V

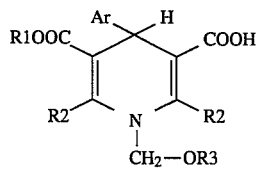

(V)

in a customary manner into the enantiomers Ia and Ib

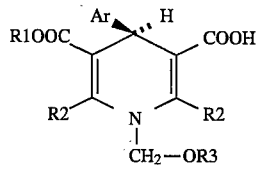

(Ia)

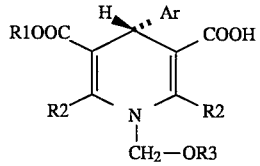

(Ib)

and employing the enantiomer Ia, after ester formation with the compound R1—X, R1 having the abovementioned meaning throughout this claim and X representing a suitable leaving group or a halocarbonyloxy group, again as the starting compound IV.

4. The process as claimed in claim 2, wherein a compound of the formula Ia is prepared in which R1 denotes 1–4C-alkyl, R2 denotes 1–4C-alkyl, R3 denotes 1–4C-alkyl, and Ar denotes 3-nitrophenyl or 2,3-dichlorophenyl.

5. The process as claimed in claim 3, wherein a compound of the formula Ib is prepared in which R1 denotes 1–4C-alkyl, R2 denotes 1–4C-alkyl, R3 denotes 1–4C-alkyl, and Ar denotes 3-nitrophenyl or 2,3-dichlorophenyl.

6. The process as claimed in claim 2, wherein a compound of the formula Ia is prepared in which R1 denotes methyl or ethyl, R2 denotes methyl, R3 denotes ethyl and Ar denotes 3-nitrophenyl.

7. The process as claimed in claim 3, wherein a compound of the formula Ib is prepared in which R1 denotes methyl or ethyl, R2 denotes methyl, R3 denotes ethyl and Ar denotes 3-nitrophenyl.

8. A process for the preparation of an optically pure 1,4-dihydropyridinemonocarboxylic acid of formula I

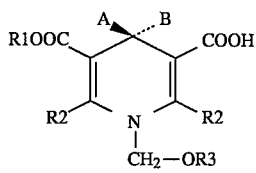

in which
R1 denotes 1–4C-alkyl,
R2 denotes 1–4C-alkyl,
R3 denotes 1–4C-alkyl or benzyl, and either
A denotes hydrogen and
B denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical, or
A denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical and
B denotes hydrogen,
which comprises hydrolysing a compound of the formula II

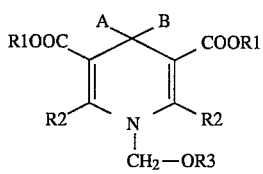

in which R1, R2, R3, A and B have the abovementioned meanings, in an alcohol R1—OH R1 being 1–4C-alkyl using aqueous alkali metal hydroxide, and resolving the resultant acid III

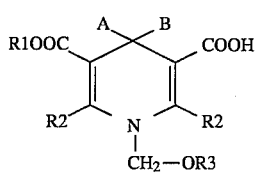

into the enantiomers in a customary manner.

9. A process for the preparation of an optically pure 1,4-dihydropyridinemonocarboxylic acid of the formula I

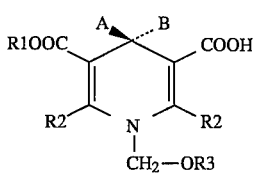

in which
R1 denotes 1–4C-alkyl,
R2 denotes 1–4C-alkyl,
R3 denotes 1–4C-alkyl or benzyl, and either
A denotes hydrogen and
B denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical, or A denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical and
B denotes hydrogen,
by partial hydrolysis of a compound of the formula II

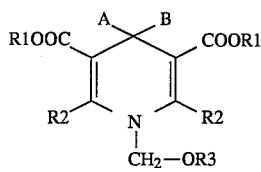

in which R1, R2, R3, A and B have the abovementioned meanings, to give an acid III

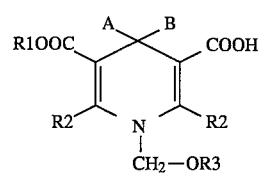

and resolution into the enantiomers in a customary manner, which comprises employing the undesired enantiomer, after ester formation with the compound R1—X in which R1 has the abovementioned meaning and X represents a leaving group or a halocarbonyloxy group, again as the starting compound II.

10. A process for the preparation of an 1,4-dihydropyridinemonocarboxylic acid of the formula III

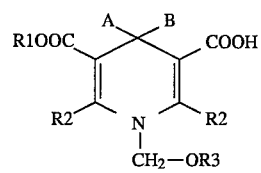

in which
R1 denotes 1–4C-alkyl,
R2 denotes 1–4C-alkyl,
R3 denotes 1–4C-alkyl or benzyl, and
A denotes hydrogen and
B denotes a 2-chlorophenyl, 3-chlorophenyl, 2,3-dichlorophenyl, 2-nitrophenyl, 3-nitrophenyl, benzoximidazolyl (4-benzofurazanyl), 2-trifluoromethylphenyl, 2,3-methylenedioxyphenyl or 2-difluoromethoxyphenyl radical,
which comprises hydrolysing a compound of the formula II

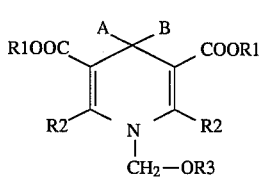

in which R1, R2, R3, A and B have the abovementioned meanings, in an alcohol R1—OH R1 being 1–4C-alkyl using aqueous alkali metal hydroxide.

* * * * *